(12) United States Patent
Herbst

(10) Patent No.: US 11,020,597 B2
(45) Date of Patent: Jun. 1, 2021

(54) METHOD AND APPARATUS FOR DIAGNOSIS AND TREATMENT

(71) Applicant: Ewa Herbst, Edgewater, NJ (US)

(72) Inventor: Ewa Herbst, Edgewater, NJ (US)

(73) Assignee: Innovations Holdings, L.L.C., Edgewater, NJ (US)

( * ) Notice: Subject to any disclaimer, the term of this patent is extended or adjusted under 35 U.S.C. 154(b) by 0 days.

(21) Appl. No.: 14/954,441

(22) Filed: Nov. 30, 2015

(65) Prior Publication Data

US 2016/0157775 A1    Jun. 9, 2016

Related U.S. Application Data

(63) Continuation of application No. 13/475,833, filed on May 18, 2012, now Pat. No. 9,199,076, which is a continuation-in-part of application No. 12/485,855, filed on Jun. 16, 2009, now abandoned, and a continuation-in-part of application No. 12/098,257, filed on Apr. 4, 2008, now abandoned, which is a continuation-in-part of application No. 11/151,967, filed on Jun. 14, 2005, now abandoned.

(Continued)

(51) Int. Cl.
| | |
|---|---|
| *A61N 1/36* | (2006.01) |
| *A61B 5/00* | (2006.01) |
| *A61N 1/372* | (2006.01) |
| *G16H 40/63* | (2018.01) |
| *A61M 5/172* | (2006.01) |

(52) U.S. Cl.
CPC ........ *A61N 1/37241* (2013.01); *A61B 5/4836* (2013.01); *A61B 5/4839* (2013.01); *A61M 5/1723* (2013.01); *A61N 1/36139* (2013.01); *A61N 1/37247* (2013.01); *G16H 40/63* (2018.01); *A61B 5/00* (2013.01); *A61N 1/36031* (2017.08); *A61N 1/37252* (2013.01)

(58) Field of Classification Search
None
See application file for complete search history.

(56) References Cited

U.S. PATENT DOCUMENTS

| | | | | |
|---|---|---|---|---|
| 2004/0122702 A1* | 6/2004 | Sabol | ................. | G06Q 50/22 705/2 |
| 2008/0004904 A1* | 1/2008 | Tran | ................. | A61B 5/0006 705/2 |
| 2008/0125634 A1* | 5/2008 | Ryan | ................. | A61B 5/01 600/342 |

* cited by examiner

*Primary Examiner* — Jon Eric C Morales
(74) *Attorney, Agent, or Firm* — Byrne Poh LLP

(57) ABSTRACT

Method and apparatus for performing multiple measurements and diagnoses include a data acquisition module, a data processing module, an optional treatment output module, a user control module, and a user display system, where the data acquisition module sends a plurality of measurement data simultaneously to the data processing module. The data processing module provides a plurality of outputs which can be made available to the user or combined in the diagnostic module. A treatment algorithm in the treatment module can affect the patient through a feedback mechanism. In response, the data processing module generates treatment information needed by the treatment output module. In one embodiment, the data acquisition module sends multiple different measurement data relating to one or more diseases to the data processing module. In response to further measurements of the parameters, an effectiveness of the treatment can be determined and the treatment regimen can be modified, as necessary.

20 Claims, 4 Drawing Sheets

Related U.S. Application Data

(60) Provisional application No. 61/129,285, filed on Jun. 16, 2008, provisional application No. 60/915,097, filed on Apr. 30, 2007, provisional application No. 60/599,959, filed on Aug. 9, 2004.

METHOD AND APPARATUS FOR DIAGNOSIS AND TREATMENT

CROSS-REFERENCE TO RELATED APPLICATIONS

This application is a continuation of U.S. patent application Ser. No. 13/475,833, filed May 18, 2012, which is hereby incorporated by reference herein in its entirety.

U.S. patent application Ser. No. 13/475,833 is a continuation-in-part of U.S. patent application Ser. No. 12/485,855, filed Jun. 16, 2009, which claims the benefit of U.S. Provisional Patent Application No. 61/129,285, filed Jun. 16, 2008, each of which is hereby incorporated by reference herein in its entirety.

U.S. patent application Ser. No. 13/475,833 is also a continuation-in-part of U.S. patent application Ser. No. 12/098,257, filed Apr. 4, 2008, which claims the benefit of U.S. Provisional Patent Application No. 60/915,097, filed Apr. 30, 2007, and which is a continuation-in-part of U.S. patent application Ser. No. 11/151,967, filed Jun. 14, 2005, which claims the benefit of U.S. Provisional Patent Application No. 60/599,959, filed Aug. 9, 2004, each of which is hereby incorporated by reference herein in its entirety.

FIELD OF THE INVENTION

The invention relates generally to analysis methods and equipment, and in particular to measurement, diagnostic, and treatment equipment able to perform any or all of the functions substantially simultaneously or in a prescribed order. It allows not only for immediate testing but also for long term monitoring of the disease, and for treatment in response to such monitoring, as well as for monitoring of treatment efficacy, which can have importance both for personalized medicine and for drug discovery.

The equipment will allow a lab or doctor not only to diagnose the patient (human or non-human (for example, a cow, sheep, horse, etc.) but also to approach each patient's needs individually (effecting truly personalized medicine) in order to:

1) be able to identify a sub-population of patients who may not be appropriate candidates for a specific treatment, either due to a predicted lack of treatment efficacy, or due to potentially significant side effects for their biological make-up;

2) allow for appropriate individual treatment dose and delivery scheme, based not only, for example, on the patient's age and weight, but also on biomarkers and other measured analytes; and 3) allow for a combination of drugs (in appropriate doses), based on the individual patient's test results.

The invention also relates generally to delivery systems that transport substances (e.g., drugs, fluids, etc.), where the delivery may be adjusted and controlled using a feedback mechanism.

BACKGROUND OF THE INVENTION

The medical device field for measurement, analysis, and treatment of the human (and non-human) condition has grown substantially over the past years as the ability to build customized equipment, easily and quickly using specialized chips has enabled both large and small companies to enter the field. Of particular interest has been the use of so-called "biomarkers", each of which can be defined to represent a specific measurement or series of measurements, representative of a specific condition or function of the human body. Such biomarkers typically relate to a biological condition, state, or function, but not measurements of seemingly unrelated parameters such as blood gases (e.g., $pO_2$, $pCO_2$), pH, electrolytes, temperature, measured bodily electrical signals (e.g., EKG, EEG, EMG), etc.

Substantial quantities of data relating to biomarkers and other parameters regarding the human condition such as blood gases, pH, electrolytes, temperature, electrical signals and the like have been collected for many specific diseases of the body. Also automatic test equipment has been marketed and has been, typically, measurement driven. Equipment is available for measuring pH, oxygen, and temperature at various parts of the body, and various biological measurement schema which are intended to measurement, for example, sugar levels, blood cell counts, the presence of various genes, proteins, acids, etc., and so on are also available. Such equipment is available from many different vendors and provides in many cases, excellent results for the measurement for which they were designed. It is then, typically, up to the doctor or an automated analysis device, which is used by the lab or the doctor and into which selected data is provided, as requested by the doctor, to provide a diagnosis of the patient.

Similar advances are being made in connection with non-human measurement and analysis, as well as in the measurement and analysis of environmental "parameters" (for example, quality of water) in an effort to improve and automate the analysis and resulting diagnosis and conclusions relating to the input data.

SUMMARY OF THE INVENTION

In accordance with some embodiments of the present invention, methods and apparatus for diagnosis and treatment are provided.

In some embodiments, an apparatus for performing multiple diagnostics simultaneously, in terms of body function, is provided, the apparatus comprising: a data acquisition module; a data processing module connected to the data acquisition module; a treatment output module connected to the data processing module; a user control module connected to the data processing module; a user display system connected to the data processing module; and said data acquisition module sending a plurality of measurement data simultaneously, in terms of body functions, to said data processing module, and in response thereto, the data processing module generates patient information needed by the treatment output module.

In some embodiments, the apparatus further comprises: said data processing module being responsive to said user control module for generating said patient information and for generating user display information for use by the user display system.

In some embodiments, the apparatus further comprises: said data acquisition module sends the plurality of the measurement data relating to a single disease to said data processing module.

In some embodiments, the apparatus further comprises: measuring modules, connected to said data acquisition module, comprising one or more of: one or more biomarker sensors, a pH sensor, a $pO_2$ sensor, a spectrometer, an optical sensor, and an electrical measurement system, a chemical measurement system, a physical measurement system, and an electrochemical measurement system.

In some embodiments, a method for performing multiple diagnostics is provided, the method comprising: simultaneously, in terms of body functions, measuring, using a data acquisition module, a plurality of parameters relating to diagnosis or treatment of a disease; in response to said measured parameters, determining said diagnosis or treatment of said disease; and effecting a treatment regimen based on said determined diagnosis or treatment.

The method further comprises: selecting a plurality of the parameters to measure in response to a user input, and displaying to said user, a diagnosis and a basis therefore.

The method further comprises: in response to further measurements of said parameters, determining an effectiveness of said treatment, and modifying, as necessary, said treatment regimen; and monitoring, on an on-going basis, the effectiveness of said treatment.

In some embodiments, an apparatus for performing multiple diagnostics simultaneously, in terms of body function, is provided, the apparatus comprising: a data acquisition module; a data processing module connected to the data acquisition module; a user control module connected to the processing module; and said data acquisition module sending a plurality of measurement data simultaneously, in terms of body functions, to said data processing module, and in response thereto, the data processing module generates patient information.

In some embodiments, the apparatus further comprises: a treatment output module connected to the data processing module.

In some embodiments, the method further comprises, in response to said further measurements of said parameters, modifying, as necessary, said treatment regimen.

In some embodiments, an apparatus for simultaneously performing multiple diagnostics is provided, the apparatus comprising: a diagnostic apparatus that performs multiple diagnostics on one or more diseases and that receives a plurality of inputs, wherein the diagnostic apparatus comprises: one or more data acquisition modules that receive at least one of: biomarker data and data from one or more other measurements; and one or more data processing modules connected to the one or more data acquisition modules that receive at least a portion of the data from the data acquisition module, wherein the data processing module responsively generates patient information relating to a patient based at least in part on the received portion of the data.

In some embodiments, the data processing module transmits the patient information to one or more of: a treatment output module for effecting a treatment, an external database for storage, and an external display.

In some embodiments, the apparatus further comprises: a communications module that communicates with the external database for at least one of: receiving the patient information, storing the patient information, and managing the patient information.

In some embodiments, the biomarker data is derived using spectroscopy. In some embodiments, the spectroscopy is selected from at least one of: fluorescent spectroscopy, mass spectroscopy, Raman spectroscopy, and Fourier transform infrared spectroscopy.

In some embodiments, the data is measured in real time and simultaneously.

In some embodiments, the one or more other measurements are received from at least one of: a pH sensor, a pO2 sensor, an optical sensor, an electrical measurement system, a chemical measurement system, a physical measurement system, and an electrochemical measurement system.

In some embodiments, a plurality of data acquisition modules receives the data from a plurality of inputs and transmits the portion of the received data to a plurality of data processing modules, and wherein each of the plurality of data processing modules transmits the portion of the data to a single processing module for subsequent processing.

In some embodiments, the apparatus further comprises a wireless communications module that communicates with an external device. In some embodiments, the wireless communications module is configured to transmit the data and the generated patient information to the external device for displaying status of the patient.

In some embodiments, the apparatus further comprises an external analysis device for diagnostic processing based on the generated patient information.

In some embodiments, an apparatus for effecting treatments upon performing one or more diagnostics is provided, the apparatus comprising: a treatment apparatus that effects a treatment regimen, wherein the treatment apparatus comprises: a treatment output module connected to a data processing module that receives patient information, wherein the patient information is derived from at least one of: biomarker data and data from one or more other measurements and wherein the treatment output module generates treatment information based at least in part on the patient information; and a feedback module connected to the data processing module that receives at least one of: updated biomarker data and updated data from the one or more other measurements, wherein the feedback module automatically controls at least one of drug delivery, electrical signal parameters, and treatment protocols in response to the updated data.

In some embodiments, the biomarker data is derived from spectroscopy. In some embodiments, the spectroscopy is selected from at least one of: fluorescent spectroscopy, mass spectroscopy, Raman spectroscopy, and Fourier transform infrared spectroscopy. In some embodiments, the one or more other measurements are received from at least one of: a pH sensor, a pO2 sensor, an optical sensor, an electrical measurement system, a chemical measurement system, a physical measurement system, and an electrochemical measurement system.

In some embodiments, the apparatus further comprises a communications module that communicates with an external database for at least one of: receiving the patient information, receiving the treatment protocols, receiving the treatment information, storing the patient information, storing the treatment information, managing patient information, managing the treatment information, and managing the treatment.

In some embodiments, the communications are conducted using a secure protocol. In some embodiments, the external database provides at least a portion of the patient information and wherein the treatment output module uses the portion of the patient information for generating the treatment information.

In some embodiments, the apparatus further comprises a wireless communications module that communicates with an external device. In some embodiments, the wireless communications module is configured to transmit at least one of: the data, the updated data, the patient information, and the generated treatment information for display. In some embodiments, the wireless communications module and the external device are configured to allow a user to manually control at least one of drug delivery, electrical signal parameters, and treatment protocols.

In accordance with some embodiments of the present invention, electronic delivery systems and methods with feedback are provided.

In some embodiments, a system for delivering a substance in a medium is provided, the system comprising: a delivery component that includes at least one reservoir, wherein the at least one reservoir contains the substance; an electronic controller that is connected to the delivery component and that controls the release of the substance from the at least one reservoir into the medium; and a sensing mechanism that monitors at least one parameter in the medium and that provides a signal to a feedback mechanism, wherein the feedback mechanism sends an electrical control signal to the controller to effect the release of the substance from the at least one reservoir into the medium.

In some embodiments, the electronic controller further comprises: at least one signal generator for generating a plurality of signals, wherein each signal has a controllable waveform based on at least one electrical parameter, and wherein the at least one electrical parameter includes any of: amplitude, frequency, shape, timing parameters, phase, pulse duration, and pulse repetition rate; a selection mechanism for selecting as output signals one or more of the plurality of generated signals; and at least one output terminal, wherein the electronic controller is configured to place at least one of the output signals on the at least one output terminal and wherein the output signals control the release of the substance from the at least one reservoir.

In some embodiments, the sensing mechanism comprises any of sensing electrodes, pickup coils, temperature sensitive devices, magnetic probes, biosensors, and biomarkers.

In some embodiments, the electronic controller is further configured to compare the monitored parameter to a desired value for the at least one parameter. In some embodiments, the desired value is one of an upper limit and a lower limit for the monitored parameter.

In some embodiments, the system is one of an electronic component, an integrated circuit, a multi-chip module, a hybrid circuit, a system-on-chip (SoC), a system-in-package (SiP), and a lab-on-a-chip.

In some embodiments, the controller is further configured to send an electrical control signal that effects the release of a given volume of the substance from the at least one reservoir.

In some embodiments, the controller is further configured to send an electrical control signal that effects the release of the substance from the at least one reservoir for a given time sequence or time pattern.

In some embodiments, in response to the sensing mechanism detecting that the concentration of the substance in the at least one reservoir is greater than a desired value, the electronic controller is configured to send an electrical control signal that effects the release of another substance into the at least one reservoir that dilutes the substance.

In some embodiments, in response to the sensing mechanism detecting that the dosage of the substance in the at least one reservoir is greater than a desired value, the electronic controller is configured to send an electrical control signal that effects the amount of the substance that is released from the at least one reservoir.

In some embodiments, the at least one parameter comprises any of pH, $pO_2$, volume, pressure, temperature, ion, dosage, time, impedance, and a biomarker.

In some embodiments, the system is a drug delivery system.

In some embodiments, a system for delivering substances in a medium, the system comprising: a delivery component that includes a plurality of reservoirs, wherein each of the plurality of reservoirs contains a substance; a controller that is connected to the delivery component, wherein the controller comprises: at least one signal generator for generating a plurality of signals, wherein each signal has a controllable waveform based on at least one electrical parameter, and wherein the at least one electrical parameter includes any of: amplitude, frequency, shape, timing parameters, phase, pulse duration, and pulse repetition rate; a selection mechanism for selecting as output signals one or more of the plurality of generated signals; and a plurality of output terminals, wherein the controller is configured to place at least one of the output signals on each of the output terminals and wherein the output signals control the release of the substance from the plurality of reservoirs; a sensing mechanism that monitors at least one parameter in the medium; and a feedback mechanism that directs the controller to effect the release of at least one of the substances from the plurality of reservoirs into the medium based at least in part on the monitored parameter.

In some embodiments, the controllable waveform comprises pulses.

In some embodiments, the at least one parameter comprises any of pH, $pO_2$, volume, pressure, temperature, ion, dosage, time, impedance, and a biomarker.

In some embodiments, the controller further comprises a combining mechanism for combining two or more generated signals to provide the output signal.

In some embodiments, the sensing mechanism comprises any of sensing electrodes, pickup coils, temperature sensitive devices, magnetic probes, biosensors, and biomarkers.

In some embodiments, the system is one of an electronic component, an integrated circuit, a multi-chip module, a hybrid circuit, a system-on-chip (SoC), a system-in-package (SiP), and a lab-on-a-chip.

In some embodiments, the plurality of signals are identical and wherein the controller is further configured to place each of the plurality of identical signals on each of the plurality of output terminals.

In some embodiments, the controller is capable of synchronizing the plurality of identical signals.

In some embodiments, the controller is arranged to independently place each of the signals on the output terminals such that each signal on each of the output terminals is independent from signals on each of the other output terminals.

In some embodiments, the controller is capable of synchronizing the plurality of independent signals.

In some embodiments, the controller is arranged to independently place each of the signals on the output terminals such that at least one of the signals on an output terminal is independent from another signal on another output terminal.

In some embodiments, the controller is capable of synchronizing the at least one signal and the another signal.

In some embodiments, the substance in one of the reservoirs is identical to the substance in each of the other reservoirs.

In some embodiments, the substance in one of the reservoirs is different from the substance in each of the other reservoirs.

In some embodiments, the substance in one of the reservoirs is different from the substance in another reservoir.

In some embodiments, the controller is further configured to send an electrical control signal that effects the release of a given volume of the substance from one of the plurality of reservoirs.

In some embodiments, the controller is further configured to: send a first electrical control signal that effects the release of a first volume of a first substance from one of the reservoirs; and send a second electrical control signal that effects the releases of a second volume of a second substance from another reservoir, wherein the first electrical signal and the second electrical signal are synchronized and wherein the first substance and the second substance are mixed.

In some embodiments, the controller is further configured to: send a sequence of control signals for at least one of delivering and mixing a plurality of substances from said reservoirs.

In some embodiments, the controller is further configured to: send a first electrical control signal that effects the release of a first volume of a first substance from one of the reservoirs; send a second electrical control signal that effects the releases of a second volume of a second substance from another reservoir, wherein the first electrical signal and the second electrical signal are synchronized; and send said control signals that effect the release of said substances in parallel or in sequence.

In some embodiments, the controller is further configured to send an electrical control signal that effects the release of the substance from one of the plurality of reservoirs for a given amount of time.

In some embodiments, in response to the sensing mechanism detecting that the concentration of the substance in at least one reservoir of the plurality of reservoirs is greater than a desired value, the controller is further configured to send an electrical control signal that effects the release of another substance into the reservoir that dilutes the substance for a given time sequence.

In some embodiments, in response to the sensing mechanism detecting that the dosage of the substance in at least one reservoir of the plurality of reservoirs is greater than a desired value, the controller is further configured to send an electrical control signal that changes the amount of the substance that is released from the at least one reservoir.

In some embodiments, a method for delivering a substance in a medium is provided, the method comprising: receiving a signal from at least one sensor, wherein the at least one sensor monitors at least one parameter in the medium; and in response to receiving the signal from the at least one sensor, transmitting an electrical control signal derived at least in part from the at least one sensor to a controller to effect the release of the substance from at least one reservoir into the medium.

In some embodiments, a method for delivering substances in a medium is provided, the method comprising: providing a plurality of reservoirs; generating a plurality of signals, wherein each signal has a controllable waveform based on at least one electrical parameter, and wherein the at least one electrical parameter includes any of: amplitude, frequency, shape, timing parameters, phase, pulse duration, and pulse repetition rate; selecting one or more of the plurality of generated signals for use as output signals; providing multiple output terminals, wherein at least one of the multiple output signals is placed on each output terminals and wherein the output signals control the release of substances from the plurality of reservoirs; monitoring at least one parameter in the medium; directing at least one controller that is connected to the plurality of reservoirs to effect the release of at least one of the substances from the plurality of reservoirs into the medium based at least in part on the monitored parameter.

In some embodiments, the at least one parameter is a biomarker.

In some embodiments, a method for delivering a substance to ectoderm-derived tissue is provided, the method comprising: receiving a signal from at least one sensor, wherein the at least one sensor monitors at least one parameter in the tissue; and in response to receiving the signal from the at least one sensor, transmitting an electrical control signal derived at least in part from the at least one sensor to a controller to effect the release of the substance from at least one reservoir to the tissue.

In some embodiments, the method further comprises: (a) generating a plurality of signals, wherein each signal has a predetermined waveform and at least one of the signals comprises pulses; (b) adjusting one or more electrical parameters of at least one signal, wherein the parameters include any of: amplitude, frequency, shape, timing parameters, phase, pulse duration, and pulse repetition rate; and (c) selecting as the control signal one or more of the generated and adjusted signals, wherein the selection is based upon an intended application.

In some embodiments, the method further comprises: (a) sensing, using one or more sensors, at least one measurable condition in the subject and providing a sensor output; and (b) adjusting one or more electrical parameters of at least one signal responsive to the sensor output, wherein the parameters include any of: amplitude, frequency, shape, timing parameters, phase, pulse duration, and pulse repetition rate.

In some embodiments, the ectoderm-derived tissue is nervous tissue, comprising at least one of brain, spinal cord, optic, and peripheral nerves.

In some embodiments, the intended stimulation application is regeneration or repair.

In some embodiments, the intended stimulation application is pain relief.

In some embodiments, the intended stimulation application is recovery or maintenance of at least one of upper and lower extremity function, bladder, bowel, and erectile function, and respiratory function.

In some embodiments, a method for delivering a substance to mesoderm-derived tissue is provided, the method comprising: receiving a signal from at least one sensor, wherein the at least one sensor monitors at least one parameter in the tissue; and in response to receiving the signal from the at least one sensor, transmitting an electrical control signal derived at least in part from the at least one sensor to a controller to effect the release of the substance from at least one reservoir to the tissue.

In some embodiments, the method further comprises: (a) generating a plurality of signals, wherein each signal has a predetermined waveform and at least one of the signals comprises pulses; (b) adjusting one or more electrical parameters of at least one signal, wherein the parameters include any of: amplitude, frequency, shape, timing parameters, phase, pulse duration, and pulse repetition rate; and (c) selecting as the control signal one or more of the generated and adjusted signals, wherein the selection is based upon an intended stimulation application.

In some embodiments, the method further comprises: (a) sensing, using one or more sensors, at least one measurable condition in the subject and providing a sensor output; and (b) adjusting one or more electrical parameters of at least one signal responsive to the sensor output, wherein the parameters include any of: amplitude, frequency, shape, timing parameters, phase, pulse duration, and pulse repetition rate.

In some embodiments, the mesoderm-derived tissue is at least one of bone, circulatory system, muscle, and urinary system tissues.

In some embodiments, the intended stimulation application is regeneration or repair.

In some embodiments, the at least one measurable condition is a biomarker.

In some embodiments, the sensor output further comprises a comparison of the sensed measurable condition and a desired value or range of values for the measurable condition.

In some embodiments, the method further comprises recording the monitored parameter and at least one of the amount, substance, and time of the effected release.

In some embodiments, the method further comprises recording the sensed measurable condition and the adjusted electrical parameters.

In some embodiments, the method further comprises repeating the measurement and comparing the new recorded information to the previously recorded information, for at least one of diagnosis or treatment.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

DESCRIPTION OF THE DRAWING

Various objects, features, and advantages of the present invention can be more fully appreciated with reference to the following detailed description of the invention when considered in connection with the following drawings, in which like reference numerals identify like elements.

DETAILED DESCRIPTION

Figure 1A:
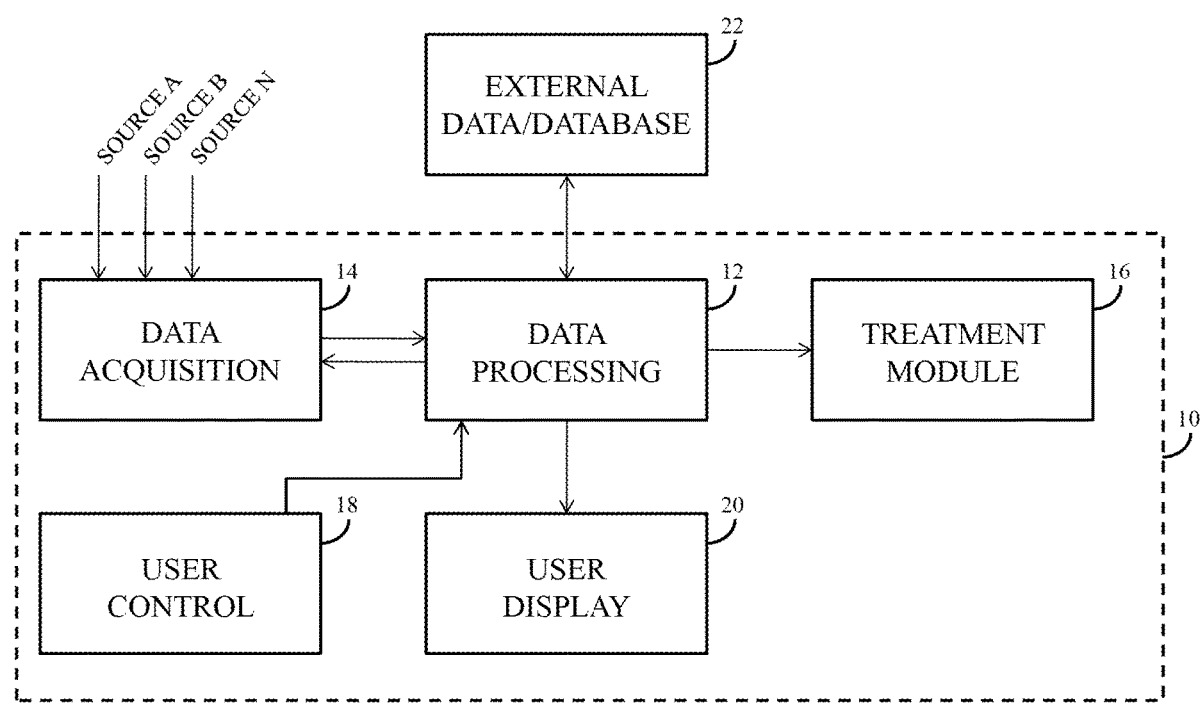
FIG. 1A is a functional blocked diagram illustrating one particular embodiment of the invention.

In the following description, numerous specific details are set forth regarding the methods and systems of the present invention and the environment in which such methods and systems may operate, etc., in order to provide a thorough understanding of the present invention. It will be apparent to one skilled in the art, however, that the present invention may be practiced without such specific details, and that certain features which are well known in the art are not described in detail in order to avoid complication of the subject matter of the present invention. In addition, it will be understood that the examples provided below are exemplary, and that it is contemplated that there are other methods and systems that are within the scope of the present invention.

Diagnosis and Treatment

Mechanisms for diagnosis and treatment are described, for example, in U.S. patent application Ser. No. 12/485,855, filed Jun. 16, 2009, which is hereby incorporated by reference herein in its entirety.

Embodiments of the invention relate to the design, use, and manufacture of a diagnostic apparatus able to perform multiple diagnostics, on the same or different diseases, within a short period of time, in terms of human body functions, instantaneously. The diagnostic equipment can use a front end, commercially available, to generate signals representative of various bio-markers, as well as signals, from the same or different sensing device (proprietary or commercial) representative of other indicia, for example of the body, not considered biomarkers as that term is currently used. Multiple discrete sensing modules or a single sensing module can be used as the front end to receive sensor signals, and the signals can be presented simultaneously or serially, to the sensing module(s), and then to a processing unit (for example, a digital signal processor (DSP)) which can be integrated into or separate from the sensing modules/devices or sensors. The analysis unit, that is, the processing unit, can have varying degrees of complexity, from a totally flexible research analysis function, incorporating user controlled, powerful processing, to one or more customized units which may or may not be user controllable, with their output being either a user defined visual, printed, audio, digital, or other presentation or signal for controlling the delivery of diagnostic information or signals, for example, for controlling the delivery of treatment directly or indirectly to or for the patient. The entire system can also be manufactured on a chip which may be a custom chip, for example, an Application Specific Integrated Circuit (ASIC), a chip preset for a class of applications, for example, an Application Specific Standard Product (ASSP), etc. The chip can be embedded in a patient, as part of a totally self-sufficient implantable device. It can also be connected either wired or wirelessly to an external viewing and communication device (desktop, handheld, or PC) allowing for a manual control of all measured parameters and treatment regimens, a data dump to the external memory or PC, and additional analysis. It can be also wired or wirelessly connected to an analysis equipment for diagnostic processing, and can be integrated into a complete stand-alone system connected to receive data from internal or external sources/sensors. The output of the chip can be interfaced with other electronic equipment, through any appropriate protocol, including secure protocols for addressing privacy concerns. While the apparatus of various embodiments can be manufactured for specific applications, that is, to check selected biomarkers and other signals for a specific disease or diseases, or other conditions, the apparatus can also interrogate a multiplicity of biomarkers, across several diseases to be examined, viewed, treated, etc., in order to provide and improve treatment outcomes due to the immediate feedback nature of the apparatus. Further, a standard set of biomarkers fitting a profile for discovering or treating a specific disease can, if appropriate, have added to it non-biomarker indicia which have the effect of improving the accuracy of the diagnosis.

Tests comprising of these markers for, for example, coronary heart disease may include cholesterol (HDL and LDL) and triglycerides combined with homocysteine and C-reactive protein (CRP), which is a general marker for inflammation and infection and PLAC testing, which in combination with LDL information is highly predictive of coronary heart disease. In an acute situation, ischemia-modified albumin and blood gases and ions will be of value. Roche Diagnostics, as an example, has a cardiac reader analyzer which allows the quantitative determination of troponin T, myoglobin, D-Dimer and now N-terminal proBNP (NT-proBNP) from a single whole blood sample within minutes.

Breast cancer tests may include CA 15-3 and CA 27.29 to follow-up breast cancer patients for reoccurrence of cancer, while ovarian cancer tests may comprise a variety of markers depending on the type of the tumor. For example, in the case of epithelial tumors, tests may comprise a combination of CA-125 (cancer antigen 125), BRCA-1 and BRCA-2, carcinoembrionic antigen (CEA), galactosyltranferase, and tissue polypeptide antigen (TPA). In the case of germ cell tumors, AFP (alpha feto protein) and quantitative hCG (human chorionic gonadotropin) can be measured, while for stromal tumors, Inhibin would be of interest.

In colon cancer, the fecal immunochemical test (FIT) or an immunochemical fecal occult blood test (iFOBT) are used. Stool DNA test looks for abnormal sections of DNA instead of blood in the stool. If results of those tests are positive, colonoscopy is required. Alternatively novel methods being developed by others rely on probe measurements which would make colonoscopy unnecessary and which could incorporate the invention.

The apparatus according to an embodiment of the invention can also diagnose, and/or treat as well as make measurements of, those bodily indicia which on their face, are uncorrelated to each other. While not obviously thereby interconnected, these measurements may, when performed substantially simultaneously (in body time) to biomarker measurements, provide insight into the nature and the occurrence of diseases as well as provide an advantage in treating diseases by correlating two or more indicia, previously considered to be unrelated.

The additional measurements may include $pO_2$, pH, temperature, pressure, electrical signals (as noted above), etc. The apparatus, according to one embodiment, can also be connected to the Ethernet or Internet to download the latest protocols, to update different levels of concern in regard to the medical measurement and diagnosis, and to provide additional or different measurements in connection with a study, such as patient data or images, for example, an MRI, CT scan, X ray.

The apparatus provides answers to the analytical questions based on inputs from biomarker and other non-biomarker signals. The analysis is primarily based on the biological/biochemical markers but can be aided by combination with non-biology input measurements such as electrical signals (e.g., EKG, EEG, EMG), chemical, physical, electrochemical, etc. When connected in a feedback configuration, the apparatus can monitor the results of treatment, in real time, to continuously or intermittently adjust and control the treatment delivery.

The invention thus relates to an apparatus for performing multiple diagnostics simultaneously, in terms of body function, having a data acquisition module, a data processing module connected to the data acquisition module, a treatment output module connected to the data processing module, a user control module connected to the data processing module, a user display system connected to the data processing module, and wherein the data acquisition module sends a plurality of measurement data simultaneously, in terms of body functions, to the data processing module, and in response thereto, the data processing module generates treatment information needed by the treatment output module.

In another aspect, the invention relates to a method for monitoring, diagnosing, and/or treatment of a disease featuring simultaneously, in terms of body functions, measuring, using a single data acquisition module, at least five parameters relating to the diagnosis or treatment of the disease, where in response to the measured parameters, the method determines the diagnosis or treatment of the disease, and effects a treatment regimen based on the determined diagnosis or treatment.

In response to further measurements of the parameters, the method determines an effectiveness of the treatment, and modifies, as necessary, the treatment regimen.

Referring to FIG. 1A, a method and apparatus in accordance with aspects of the invention include a system 10 having various modules or partitions. The system 10 can be modeled after/or be the same as, in many ways, the system on a chip described in U.S. patent application Ser. No. 12/113,200, filed on Apr. 30, 2008, now U.S. Pat. No. 7,937,683, entitled Method and Apparatus for Configurable Systems, the contents of which are incorporated herein by reference in their entirety.

Referring to FIG. 1A, again, the data processing element 12, for example a digital signal processor, a custom data processor, or any other type of data processing unit, acts as the central processing module for the system 10. In this embodiment, the processing element 12 connects to a data acquisition module 14, a treatment output module 16, a user control module 18, and a user display system 20. At a high level, in operation, the data processing module 12 receives measurements and data in the form of, for example, biomarker and non-biomarker data from the data acquisition unit, which is operating under the control of the data processing element 12. The data processing element processes that information, using, if appropriate, further information and data received from an external database or other external unit 22, and in response to user commands from a user control module 18 can generate, as required, both user display information for the user display 20 and treatment information as needed for treatment module 16. If the apparatus is embedded in the patient, it can be connected by hard wired cables, or wirelessly, continuously or intermittently, as necessary. In this exemplary configuration, a visual user display, for example, need not be used or provided. It can be, however, connected preferably wirelessly to an external monitoring unit or PC for display of the patient's status and for communication and manual control of the system, if required.

The data acquisition module 14 receives data from many different sources, for generating biomarker information as well as non-biomarker data. Biomarkers may be associated for a particular disease, or for a range of diseases, or alternatively for a series of predefined biomarkers as dictated by the user. Methods such as genomics, proteomics, and/or molecular imaging, among other methods, can be used in the generation of the biomarker information. Among specific methods used, variety of spectroscopic methods can be applied, such as fluorescent spectroscopy, mass spectroscopy, which can be used, e.g., for gene expression profiling, Raman spectroscopy and lately Fourier transform infrared spectroscopy (RTIR). The various sources then, illustrated as source A, source B . . . source N, can be sources of data associated directly with measurements made in a patient, such as, for example, temperature, pH, $pO_2$, etc. as described previously, for the non-biomarker data or data provided directly from the patient or from test results relating to biological functions and useful for determining biomarker information. Such data can be obtained as described in the art, and, more particularly, as described in, for example, applicant's U.S. Pat. Nos. 6,021,347, 6,029,090, 6,684,106, 6,708,066, 7,160,241, 7,526,334, 7,517,311, 7,937,683, 8,365,122, and 8,595,672, U.S. pending patent application Ser. Nos. 11/063,195, 11/151,967, 11/213,050, 12/098,257, 12/431,730, 12/485,855, 12/507,506, 13/085,366, 13/152,242, 13/751,274, and 14/068,792, and International Publication No. WO 2010/065678 A1, the disclosures of which are hereby incorporated by reference in their entireties.

Once the system operator has indicated which data to acquire and use, or which disease or diseases, or other conditions, to acquire data for, the data processing system then operates upon that data, in connection with its own internal memory as well as memory available to it in the form of external data or a database 22, to generate either user display information in oral, written, or display form, or any other form, needed or required by the user, and/or further, upon user control of user control module 18, the system can provide feedback, for example, to the patient in the form of treatment. Such feedback, in the form of treatment, allows for substantially automatic (or user controlled) feedback to regulate the delivery of drugs, or electronic signals, or other treatment protocols, which may then result in revised data from data acquisition module 14, thereby setting up a feedback control loop operating in response to user control, and, if desired, viewable on user display 20, as processed by data processing element 12 and implemented by the treatment module 16. Such treatment can be automatic (using feedback) and may be that described in the above-identified delivery application U.S. Ser. No. 12/098,257, or in applicant's other related patent applications, such as U.S. patent application Ser. No. 12/113,200 filed on Apr. 30, 2008, now U.S. Pat. No. 7,937,683, the contents of which are incorporated herein, in their entirety, by reference. The system can be set up (including inputs, outputs and feedbacks), data acquisition can be controlled, measurements can be processed, diagnostic or treatment algorithms can be applied and various communications schemes can be provided by, e.g., the systems described in patent application U.S. Ser. No. 61/119,244, filed on Dec. 2, 2008, the content of which is incorporated herein, in its entirety, by reference.

Thus, treatments can be either manual and/or automatic, and made more patient-related as the system reacts to the responsiveness and effectiveness of the treatments, to modify the treatments. In this regard, the signals from the external sources can be substantially simultaneous with regard to the human body's "time constant" for change and thus, all measurements can be treated as made at the same time, so long as the measurement device does not adversely interact with the measurement itself. In a specific embodiment, the measurements are made in real time and simultaneously. With such a substantial amount of data available to the data processing element 12, the system can effect diagnosis of patient concerns faster, and more accurately than prior systems which were directed to a particular type of measurement and analysis and small group of predetermined biomarkers which may or may not relate to many or any specific diagnoses/diseases. In the current apparatus, as described, the system can either collect a broad range of biomarker and non-biomarker information, substantially and preferably simultaneously as defined herein, in order to process the data and yield a result which relates to a probable diagnosis relevant to a patient's concerns and complaints. Alternatively, if the diagnosis is to relate to a specific disease, for example, breast cancer, ovarian cancer, coronary artery disease, or colorectal cancer, to name a few, a selected group of biomarker and non-biomarker measurements can be made, substantially simultaneously, in order to better diagnose the status of, and define the treatment for, such a disease in the patient.

In operation, then, the system 10 initially operates to monitor and define, based on the inputs available to it, a disease, or provide a diagnosis through a specifically developed diagnostic algorithm. The user defines different inputs, typically available in parallel, usually not from the same sensing device, in a user-friendly manner and environment. The output is either a separate measurement or a set of separate measurements provided for each sensor/biomarker or a combined diagnosis, based on the inputs available, which can be taken to the "next level" wherein a treatment regimen is determined and prescribed. A display is provided illustrating the diagnosis and the basis therefor. Other information is provided to the user. In addition, information can be provided to an internal and/or external database to provide better patient management for future efforts.

The resulting device can be used in different configurations for both standard and acute measurements and treatment, for example, in one configuration for a yearly standard health screening and in another for the emergency room, intensive care, or ambulance use. An additional application area, with possibly specific configuration, could be for emergency situations on passenger air planes and at the airports, where medical personnel may not be available.

As noted above, the invention will also be useful with non-human patients, as well as in measuring and "treating" the environment. In that respect, the specifics of the measurements and their timing may be altered depending upon the specific conditions being tested and treated.

Other objects, features and advantages of the invention will be apparent to those practiced in the field and are within the scope of the invention.

Electronic Delivery Systems and Methods with Feedback

Electronic delivery systems and methods with feedback are described, for example, in U.S. patent application Ser. No. 12/098,257, filed Apr. 4, 2008, which is hereby incorporated by reference herein in its entirety.

In accordance with some embodiments of the present invention, delivery systems and methods for delivering a substance in a medium, e.g., blood, saliva, other body fluids, muscle, etc., are provided.

In some embodiments, the delivery system includes a delivery component that includes at least one reservoir. The reservoir contains a substance (e.g., a liquid, a drug, etc.). The delivery system also includes an electronic controller that is connected to the delivery component and that controls the release of the substance from the at least one reservoir into the medium. The delivery system also includes a sensing mechanism (e.g., one or more sensors, one or more biomarkers, etc.) that monitors one or more parameters in the medium and provides a signal to a feedback mechanism. The feedback mechanism, in response to the signal, sends an electrical signal that directs the controller to effect the release of the substance from the reservoir into the medium.

In another embodiment of the present invention, the delivery system may include a delivery component that has a plurality of reservoirs. A controller that is connected to the delivery component includes a signal generator, a selection mechanism, and a plurality of output terminals. The signal generator generates a plurality of signals. Each signal has a controllable waveform based on one or more electrical parameters (e.g., amplitude, frequency, shape, timing parameters, phase, pulse duration, and pulse repetition rate). The selection mechanism selects as output signals one or more of the plurality of signals generated by the signal generator. The controller is also configured to place at least one of the output signal on each of the output terminals. It should be noted that the output signals control the release of the substance from the plurality of reservoirs. It should also be noted that each reservoir may contain a different substance. The delivery system may also include at least one feedback mechanism that directs the controller to effect the release of at least one of the substances from the plurality of reservoirs into the medium.

Because the delivery system may be controlled by the controller and the feedback mechanism, the delivery system is capable of precision mixing of various fluids or drugs (e.g., flow control of substances contained in multiple reservoirs), time delivery synchronization (e.g., daily doses, intermittent, maintenance of treatment on a daily basis, or administer the substance when needed, etc.), volumetric control of substances, synchronization for multiple substances, diluting substances for providing the appropriate dose, controlling different ports, etc.

Generally speaking, the present invention is directed to methods and systems for delivering substances (e.g., drugs, fluids, etc.), where the delivery may be automatically controlled using an electrical stimulator component and/or a feedback mechanism.

The delivery system generally includes a waveform or pulse generator circuit (e.g., a digital pulse generator, an electrical stimulator component, etc.), one or more sensors, and at least one feedback mechanism (e.g., a closed feedback loop, an open feedback loop, etc.). The sensors (e.g., physical sensors, chemical sensors, biochemical sensors, etc.) detect and/or monitor various conditions in a medium (e.g., prevailing in the tissue, existing in a system, etc.) and provide the detected information to the feedback mechanism. In turn, the feedback mechanism may direct the controller to perform an operation in response to the detected information (e.g., open a reservoir or release a given amount of drugs using an electrical, mechanical, optical, or other signal). For example, the electrical stimulator component may adjust the signal generated by the electrical stimulator component to maintain an optimal operating or treatment condition. In particular, the electrical stimulator component may adjust the signal generated to maintain a given level of, e.g., ion, salt, pH, pO2, biochemical marker, volume, dosage, etc. or a gradient thereof. When used for treatment or other suitable biomedical applications, such an adjustment may optimize the outcome of the treatment.

As used herein, "biochemical marker," which may be used interchangeably with "biological marker" or "biomarker," refers to a characteristic that is measured and evaluated as an indicator of a biological process (e.g., a normal biological process, a disease or abnormal condition, or a response to a pharmacologic or other therapeutic treatment or procedure for drug discovery). Such biomarkers may include, but are not limited to, single nucleotide polymorphisms, gene expression patterns, proteins, peptides, and small molecule metabolites (e.g., glucose, cholesterol, phospholipids, amino acids, vitamins, etc.).

The delivery system of the present invention may be used for a number of clinical applications, such as, for example, peripheral nerve regeneration, spinal cord regeneration, bone healing, wound healing, cancer treatment, cardiac rhythm management, an artificial pancreas, drug delivery, stem cell delivery, or pre-treated stem cell delivery (e.g., using the electrical stimulation systems to effect the stem cells or gene therapy), in addition to the neurological and functional electrical stimulation applications.

In some embodiments, the delivery system may be used for bone healing. Electrical stimulation of bone healing has been used clinically for more than about three decades. One approach for bone healing may include using implantable devices for both long bone healing and for spinal fusion. By controlling the electrical potential of the stimulating electrode (cathode) to be below the hydrogen evolution level, the optimization of the bone formation process may be achieved. This may be accomplished by measuring pH in the immediate vicinity of the cathode (which indicates if the hydrogen evolution takes place) and adjusting the electrical potential of the stimulating electrode accordingly.

In another suitable embodiment, the delivery system may be used for the electrochemical treatment of cancer. Prior methods that were developed originally in Sweden and used in treatment of thousands of patients in China deliver electric current to solid superficial tumors via several indwelled electrodes. The generated current destroys the tumor without any extensive bleeding by causing necrosis of the tissue and significantly changed pH values in the tissue. However, an improved method for the electrochemical treatment of cancer may be provided by automatically adjusting the electrode potential based at least in part on a measured pH value in the tissue to result in a smaller but sufficient pH changes to affect the tumor, thereby minimizing serious necrotic and inflammatory reactions.

It should be noted that, in some embodiments, electrical stimulation may be provided on demand. Electrical stimulation may be used for tissue regeneration, for recovery or maintenance of function (e.g., upper and lower extremity function, bladder, bowel, and erectile function, and respiratory function, which may be impaired in connection with, e.g., spinal cord injury, stroke, head injury, cerebral palsy, or multiple sclerosis), as well as for cardiac rhythm management. In all of those cases some disease-specific or therapeutic response-specific physical, chemical, or biochemical markers may be measured, resulting in on-demand delivery of a specific sequence of an electric signal from an external or implantable device. In the case of implantable devices, electrical stimulation may be administered as needed over a long period of time, initially to promote tissue regeneration or return of function and, at a later time, to maintain it.

In yet another suitable embodiment, the delivery system may be used to provide controlled, active drug delivery. External or implantable drug delivery systems may be automatically controlled by electrical signals received in response to appropriate physical, chemical, or biochemical markers continuously or intermittently monitored in the tissue. A waveform generator may be used to control both the drug delivery timing sequences and a sensor measurement sequence, if intermittent. Sensor information may trigger the drug delivery mechanism, when, for example, the measured parameters fall outside of a given optimal value range (e.g., a preset optimal value range). For example, an example of a specific application may be an insulin pump.

Alternatively, the delivery system of the present invention may be used to deliver fluids or other suitable substances (e.g., through catheters, IV, or microfluidic channels). For example, the delivery system may be fabricated or integrated onto a System-on-a-Chip (SoC). In addition, sensors, an electrical stimulator, a microprocessor (if needed) for controlling various components on the SoC, and/or any other suitable component may be integrated onto the delivery system, which may be implemented as a system on the chip.

For example, microfluidic devices may be used in printheads and other components of an inkjet printer. The present invention may be used to control the delivery of ink at the micron scale. As described above, each device may be electrically controlled using the delivery system of the present invention. In response to receiving an electric or optical signal a reservoir may open, allowing ink to flow through one of the channels in the inkjet printhead. The system can be also used for delivering antibodies, etc. for "diagnostic arrays" or "lab on a chip".

In some embodiments, the delivery system of the present invention may be used in a high pressure liquid chromatography (HPLC) system. While HPLC has provided a separation tool capable of high resolution separations, rapid analysis, and high sensitivity, obtaining all the benefits that HPLC offers typically requires careful attention to the flow portion of the HPLC system that carries the sample. Limitations on the performance of the HPLC system are generally caused by problems with fluid transfer (e.g., dead volume, volume is different in certain columns, etc.). In many cases, the smallest amount of dead volume in the HPLC system may make the difference between an acceptable separation and an unacceptable one. Dead volume dilutes chromatographic peaks, increasing their volume and reducing chromatographic efficiency. Accordingly, the delivery system of the present invention may be used in a HPLC system to control the flow of fluids throughout the system, thereby reducing the amount of dead volume in the HPLC system.

In some embodiments, the delivery system of the present invention may be used in a bioreactor. A bioreactor is generally a vessel or contained area in which a chemical process that involves organisms or biochemically active substances derived from such organisms is carried out. In particular, the environmental conditions within the vessel of the bioreactor, such as gas (e.g., air, oxygen, nitrogen, carbon dioxide), flow rates, temperature, pH, dissolved oxygen levels, and agitation speed need to be closely monitored and controlled. The delivery system may be integrated or connected to the bioreactor to monitor and control the environmental conditions in the bioreactor.

It should also be noted that although the present invention is described in terms of a delivery system, this is only one embodiment. The present invention may also be used in analytical instrumentation, in automatic test equipment, for drug discovery, or any other suitable application.

Figure 1B:
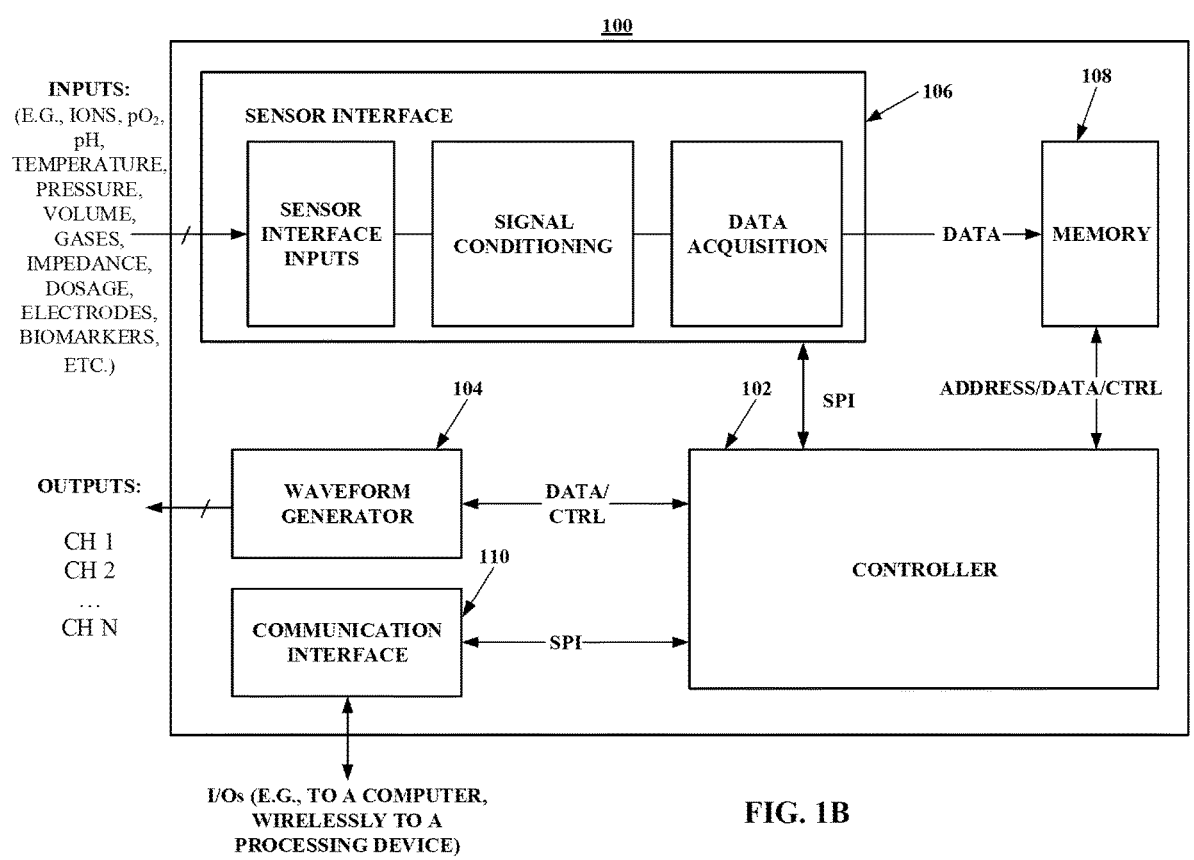
FIG. 1B shows a schematic diagram of an illustrative system suitable for delivering a substance (e.g., drugs, liquid, etc.) or electrical stimulation and having feedback capabilities in accordance with some embodiments of the present invention.

FIG. 1B shows a schematic diagram of an illustrative system suitable for delivering a substance (e.g., drugs, liquid, etc.) or electrical stimulation and having feedback capabilities in accordance with some embodiments of the present invention. As shown in FIG. 1B, delivery system 100 includes a controller 102 (e.g., a microprocessor or any other suitable processing device), a waveform generator 104, and a sensor interface 106.

In some embodiments, delivery system 100 may also include memory 108 and a communication interface 110. Communication interface 110 may be any communication link suitable for communicating data between delivery system 100 and a computer (e.g., a workstation, PDA, laptop computer, cellular telephone, etc.), such as a network link, a dial-up link, a wireless link, a hard-wired link, etc.

In some embodiments, waveform generator 104 may be a digital pulse generator Application Specific Integrated Circuit (ASIC). In some embodiments, waveform generator 104 may be an electrical stimulator component (sometimes referred to herein as an "ES component") with one or more output stages.

In general, an electrical stimulator component includes an ES signal stage having a selector coupled to a plurality of different signal generators, each producing a signal having a distinct shape such as a sine, a square or sawtooth wave, or a simple or complex pulse, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. In some embodiments, also included in the system may be a measuring stage which measures and displays (if needed) the electrical stimulation signal operating on the substance being treated as well as the outputs of various sensors which sense conditions prevailing in this substance, whereby the user of the system can manually adjust it or have it automatically adjusted by feedback to provide an electrical stimulation signal of whatever type he wishes and the user can then observe the effect of this signal on a substance being treated.

Figure 2:
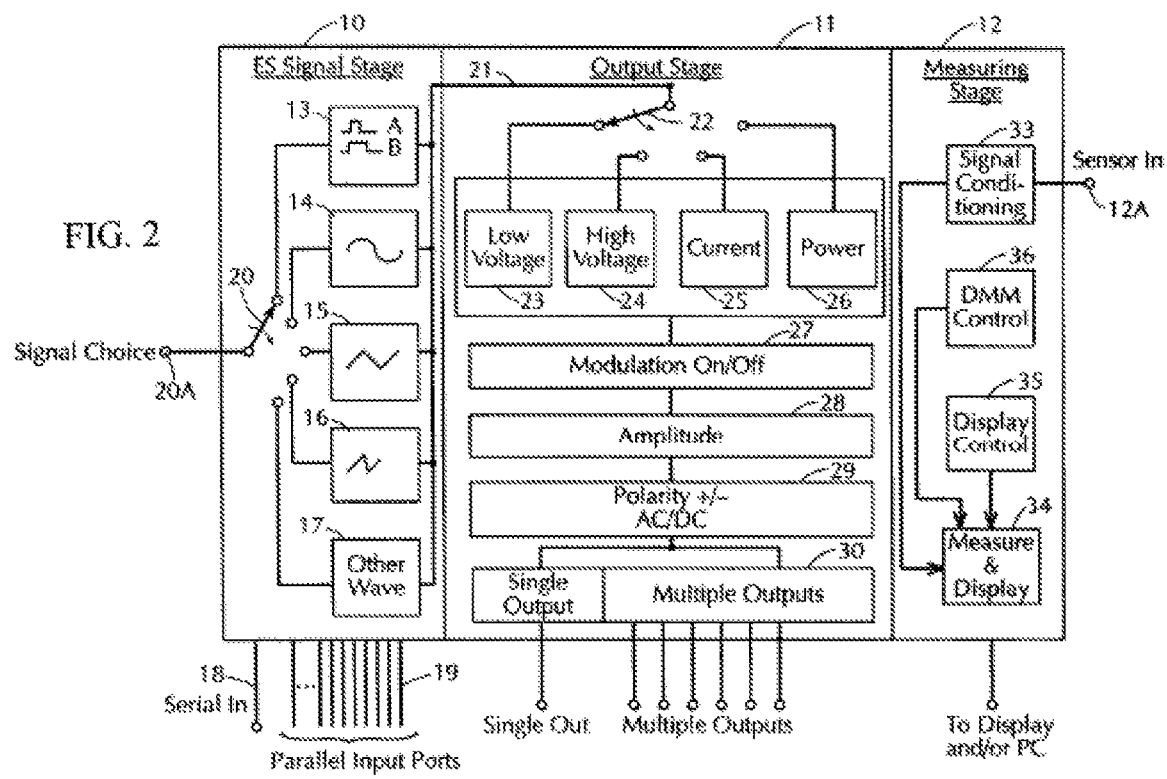
FIG. 2 is an illustrative block diagram of an exemplary electrical stimulation system having an ES stage, an output stage, and a measuring stage that may be used in accordance with some embodiments of the present invention.

An electrical stimulator component or system in accordance with the present invention is shown in FIG. 2. The electrical stimulator system is composed of an ES signal stage 10 which at the user's discretion generates a faradic, an electromagnetic, or other type of electrical stimulation signal which is fed to an output stage 11. Output stage 11 processes the electrical stimulation signals selected by the user to yield a stimulation signal suitable for its intended biological or bio-medical application.

Also provided is a measuring stage 12 which measures and displays the electrical stimulation signal operating on the biological substance being subjected thereto, and/or its electrical parameters as well as the output of various sensors which sense conditions prevailing in this substance whereby the user is able to observe, monitor as well as to adjust the effects of the stimulation signal he has selected on the substance being treated.

ES signal stage 10 includes signal generators 13 to 17 producing signals of different shape. Generator 13 is a pulse wave generator generating one or more rectangular pulses, such as pulses A and B of different width which can be outputted separately or can be added or subtracted from each other to yield A or B, A plus B or A minus B. Generator 14 is a sine wave generator, generator 15 generates a triangular or sawtooth wave, and generator 16 produces a ramp voltage wave. Generator 17 yields a wave of any arbitrary shape. The signal generators are capable of generating a minimum one pulsatory signal or a greater numbers of pulsatory signals, or of generating a gated signal with a minimum of one period or a greater number of periods, with individual adjustments of electrical parameters.

By means of a serial input port 18 to ES stage 10 or a set of parallel input ports 19, the parameters of the respective waves produced by signal generators 13 to 17 can be adjusted in frequency, pulse width, amplitude and repetition rate, or with respect to any other variable. Coupled to generators 13 to 17 and activated by a signal applied thereto at terminal 20A is a mechanical, electronic, or optical, etc. (e.g., nanomaterial) selector switch 20. The output signal from the signal generator selected by a switch 20 is applied through a line 21 to output stage 11. In practice, the line is preferably a bus system.

The ES signal stage 10 is preferably miniaturized and may take the form of a hybrid device or a single ASIC chip (Application Specific Integrated Circuit). Output stage 11 includes a mechanical, electronic, or optical selector switch 22 which applies the ES signal from stage 10 either to a low voltage processor 23, a high voltage processor 24, a current processor 25, or a power processor 26 to put the ES signal in a form appropriate to the intended application for electrical stimulation. In a preferred version, all signals can be accessed simultaneously by one or more output stages through a system bus. In practice, a combination of one or more signal generators in the ES signal stage with one or more of the output stages can be miniaturized.

The output of the processor 23, 24, 25 or 26 chosen by selector switch 22 is fed to a modulator 27 coupled to an amplitude control unit 28 which modifies the amplitude of the signal applied thereto. (There are also other ways to control the amplitude.) The output of amplitude-control unit 28 is applied to a polarity control unit 29 in which the electrical stimulation signal is given a positive or negative polarity or is converted to an AC signal, depending on the intended application for the electrical stimulation signal.

Each output stage can be configured with either multiple output terminals 30 or with a single output. The multiple outputs make it possible to run several parallel experiments or processes concurrently.

Figure 3:
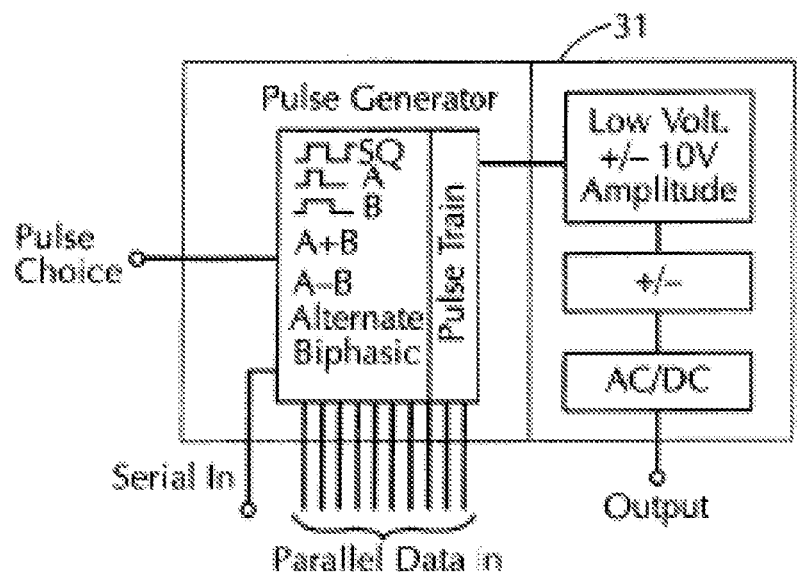
FIG. 3 is an illustrative block diagram of a basic version of a system for producing various electrical stimulation pulses that may be used in accordance with some embodiments of the present invention.
Figure 4:
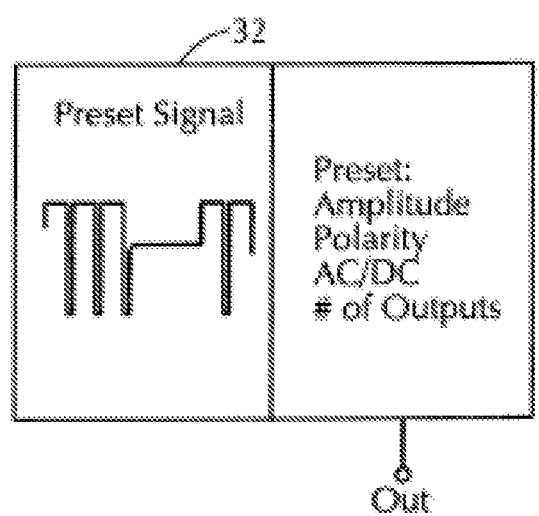
FIG. 4 is an illustrative example of a preset custom module that may be used in accordance with some embodiments of the present invention.

As previously mentioned, the ES system can be miniaturized to form a single ES component comprising signal generators and miniaturized output circuitry packaged together. A functional sketch of one such ES component 31 is shown in FIG. 3, and an example of a customized module 32 with a preset waveform and preset electrical parameters is shown in FIG. 4.

A preferred version of the ES component includes a sophisticated digital pulse generator on a chip and an analog circuitry to define complex pulse patterns, with amplitudes appropriate for a given application. The output can be fed into any number of desirable output stages, which can be integrated into the same component or be independent proprietary devices, e.g., voltage controlled or current controlled output stages with various voltage/current amplitudes, high frequency output stage with various bandwidths depending on a specific application, various power output stages, etc. Waveforms other than pulse patterns, as well as modulated signals can be part of such a "system on a chip."

The design of a digital pulse generator (which can be implemented, e.g., as an ASIC) consists of several blocks, which can be either used together to create a sophisticated pulse generator for biomedical applications, or can be used in any number of other applications requiring a pulse signal. Each of these blocks or functional modules can provide an independent waveform or pulse (A pulse; B pulse; square wave; time delay; etc.). A basic one output version of the signal generator delivers two independent pulses A and B with digitally adjustable pulse widths, the same pulse repetition rate, and with an adjustable delay between them or for each of them. It also delivers a square wave and timing for alternate and biphasic pulses and two pulse trains. In a two or more output version, individual pulses can have independently set repetition rates.

Several of these independent signal generators can be combined into a multi-output device. All timing parameters of the pulses preferably are fully programmable by a user via hardware or via software. For example, one can adjust timing using thumbwheels or switches connected via parallel inputs of the ES component, or by using software and a serial, parallel, or custom interface as an input (or a combination of analog and digital inputs can be used). The ES component can include both a parallel and a serial interface so that the user can define the optimal means for each application.

The analog output amplitudes of the ES component or ES system can be adjusted for each pulse separately (via hardware or software, as above). At the same time, a specific DC level can be added; i.e., signal can be shifted up or down from zero line. The alternate and biphasic pulses are designed so that only one adjustment for both positive and negative pulse width and amplitude is required, which results in guaranteed symmetrical signals.

Electric stimulator components, multi-functional systems, and methods for generating output signals are described, for example, in above-mentioned U.S. Pat. No. 6,684,106, which is hereby incorporated by reference herein in its entirety.

Referring back to FIG. 1B, delivery system 100 may also include a feedback mechanism. One or more sensors may be connected to delivery system 100. The sensors may be used to measure and/or detect various conditions prevailing in the tissue or any suitable medium. Sensor interface 106 may include any component necessary to monitor and analyze data received by the sensors. For example, as shown in FIG. 1, sensor interface 106 includes signal conditioning circuitry and data acquisition circuitry. In response to receiving a signal from a sensor, the feedback mechanisms may use the information relating to, for example, the pH level, the pO2 level, the volume of drugs distributed, the drug dosage, timing parameters for drug delivery (e.g., time-released, delayed release, etc.), or any other suitable parameter and direct the stimulator, the controller, or any other suitable component of delivery system 100 to perform an operation. For example, the stimulator may use at least a portion of the information to adjust its signal accordingly to maintain an optimal level of measured entity (e.g., pH, pO2, ion concentration, biochemical marker, pressure, temperature, etc.) and to optimize the treatment outcome. In particular, the sensor capability and a feedback loop allow a user to measure or to measure automatically the effects of electrical stimulation on the tissue under treatment and also to adjust the level, the type of the electrical stimuli, and/or any other suitable parameter to optimize the treatment outcome. Using the drug delivery system, external or implantable devices for drug delivery may also be controlled.

It should be noted that the delivery system of the present invention is also capable of analyzing and/or controlling linear and non-linear processes, such as flow, pressure, temperature, and pH. For example, the delivery system of the present invention may include an adaptive controller or a model free adaptive controller. In cases where proportional-integral-derivative (PID) controllers may not be able to handle large dynamic changes (e.g., the logarithmic changes of pH), the model free adaptive controller may be used.

In some embodiments, the electrical stimulator component of the delivery system may be used to control the delivery of drugs, fluids, or other substances. Using the electrical stimulator component, several, simple or complex rectangular pulses and other signals are available, for the output stages, through a selector or preferably on a bus. These signals are synchronized and may be accessed by an output stage either by selecting only one signal or by accessing several signals at the same time. In the latter case, the signals may be combined in the output stage to a more complex pattern. In either case, they may be accessed by a single selected output stage or simultaneously by several, either identical or different, output stages.

For example, the electrical stimulator component may include a signal generator that generates multiple signals, where each signal has a controllable waveform based on one or more electrical parameters (e.g., amplitude, frequency, shape, timing parameters, phase, pulse duration, and pulse repetition rate). The electrical stimulator component may also include a selection mechanism to select as output signals one or more of the signals generated by the signal generator. These output signals are placed on one or more output terminals. For example, multiple signals (e.g., a combined signal) may be placed on a single output terminal. In another example, identical signals may be generated and placed on different output terminals. In yet another example, different signals may be generated using the signal generator and placed on different output terminals. The output signals control the release of the substance from the reservoirs connected to the delivery system.

It should be noted that the electrical stimulator is configurable such that the delivery of substances in reservoirs connected to the delivery system may be synchronized and/or preset (e.g., daily doses, intermittent, maintenance of treatment of a daily basis, etc.), fluid flow from reservoirs may be controlled such that precision mixture of various substances (e.g., fluids or drugs) may be attained, substances may be time delayed or time released, substances may be volumetrically controlled, substances may be diluted to provide an appropriate dosage, etc. For example, the electrical stimulator may be configured to generate two identical signals on different output ports that control reservoirs containing different substances. Upon receiving the identical signals, the delivery system may synchronously dispense two different substances at the same time.

Using the electrical stimulator component, the delivery system may be used for a number of applications when combined with different output stages. The delivery system may be used as a controller in an automatic external or implantable drug delivery device. The delivery system may be preset with predefined signal patterns for specific application or for double blind studies, thereby eliminating the need to continuously develop new experimental systems at a larger cost.

The electrical stimulator component may be integrated in or connected to an external or implantable device that holds a given amount of drugs, fluids, or any other suitable substance (e.g., in one or more reservoirs). For example, electrodes that are connected to the electrical stimulator component may be implanted in a tumor or placed in its immediate vicinity and current is caused to flow therethrough between the electrodes in the course of which a cytotoxic agent is synthesized in situ by a reaction between the material of the electrode and a substance delivered to the tumor.

In practice those or other reactions may take place between the electrode and the reagent introduced into the tumor, with a hollow electrode or a catheter used for delivery, or between two or more substances either naturally occurring in the organism or introduced into the tumor, with the electrode having an electrocatalytic effect. The material of the electrode controls the course and/or the speed of reactions whose products are cytotoxic.

One way of carrying out a method is by potential-controlled reaction at the electrodes implanted in the tumor. Another way in accordance with the invention is by using hollow electrodes or a catheter for adding an appropriate substance to ensure the proper chemical environment for the formation of the cytotoxic agent in situ. Still another way is by continuously or intermittently releasing in situ from an implanted reservoir (one embodiment is a hydrogel capsule, as described below) appropriate substances to ensure the proper chemical environment for the formation of the cytotoxic agent in situ. Such time released substances, activated electrically when needed, can be applied over extended periods of time including a period after the main treatment has been completed, to prevent a reoccurrence of cancer. These can also be used to activate the immune system response.

The same method can be used to produce in situ non-cytotoxic agents, which can later be converted to the cytotoxic agents by isomerization. Isomerization is a process whereby a compound is changed into one of its isomers; i.e., one of two or more chemical substances having the same elementary percentage composition and molecular weight but differing in structure, and therefore in properties. An example thereof is transplatin and cisplatin. While cisplatin is highly cytotoxic, transplatin is considered not to be.

Because the synthesis process is electrically-assisted and because the electrical stimulator component is configurable (e.g., amplitude, frequency, shape, timing parameters, phase, pulse duration, and pulse repetition rate), the electrical stimulator component of the delivery system may be used to control the amount of cytotoxic agent, which is synthesized.

Additional systems and methods for in situ electrochemical treatment of a malignant tumor, which destroys the tumor with minimal damage to regions surrounding the tumor, are described further in commonly-owned, commonly-assigned U.S. Pat. No. 6,708,066, which is hereby incorporated by reference herein in its entirety.

In some embodiments, the delivery system of the present invention may be used to automatically control the release of various substances from a device, such as an implantable device. For example, an implantable reservoir carrying one or more drugs, fluids, or other suitable substances may be automatically controlled by means of electrical modulation of the material properties of the walls of such a reservoir, for example a hydrogel capsule, or by controlling a micro pump, e.g., an insulin pump with an appropriate time sequence of an electric signal.

In some embodiments, the sensors used in the delivery system may be hydrogel biosensors. Hydrogel biosensors (such as those developed by M-Biotech, Inc. of Salt Lake City, Utah) may be used for the continuous monitoring of various substances, such as, for example, salt, pH, temperature, alcohol, amino acids, flavors, penicillin etc. Each hydrogel biosensor generally consists of two parts: a hydrogel and a miniature pressure transducer. In case of a glucose biosensor, the hydrogel either swells or contracts as a function of glucose concentration changes in the body fluid. A pressure transducer is used to measure the changes in the swelling of the hydrogel. A resulting voltage signal (in mV) is produced on the output of the transducer.

In some embodiments, the sensors used in the delivery system may be self-assembling hydrogels or any other suitable self-assembling substance. These self-assembling hydrogels may include two materials (e.g., fluids) that remain separate until, for example, a given pH level is reached. Upon reaching that pH level, the two materials self-assemble into a hydrogel. This pH-dependent hydrogel may also disassemble at a specific pH level. These self-assembling hydrogels may be used as configurable membranes or reservoirs for drug delivery. For example, upon connecting the delivery system to control a self-assembling hydrogel, the delivery system may be used to control the pH level of the hydrogel such that at a given pH (or other suitable parameter), the hydrogel assembles preventing and/or significantly reducing the amount of drugs or any suitable substance released to the area where the hydrogel is located. Similarly, a given pH may be attained such that the hydrogel dissembles at predefined pH and allows the drugs or any suitable substance to be administered. The delivery system having the electrical stimulator may be used to control the permeability of a given area or delivery port.

For example, a number of self-assembling hydrogel reservoirs may be fabricated. Upon connecting each output port of the electrical stimulator component or any other suitable component to each self-assembling hydrogel reservoir, the delivery system is capable of controlling the release of each of the substances contained in each reservoir (e.g., each reservoir contains 1 mL of a given drug and when 4 mL of the drug are needed, four output signals are transmitted through the output ports to effect the release of four reservoirs).

In another suitable example, the reservoir may be made of any suitable material, where the reservoir has an opening (having a given dimension) made of the self-assembling hydrogel. For example, an electrode may be weaved through the self-assembling hydrogel such that the assembling and disassembling of the hydrogel may be electrically controlled. By controlling the hydrogel opening, the reservoir may release a given amount of drugs for a predefined amount of time.

In the example of treating tissues, such as a malignant tumor, a hydrogel capsule may be used to continuously or intermittently release in situ from an implanted reservoir appropriate substances, such as drugs, to ensure the proper chemical environment for the formation of the cytotoxic agent in situ. Such time released substances, activated electrically when needed, may be applied over extended periods of time including a period after the main treatment has been completed to prevent a reoccurrence of cancer.

Accordingly, in some embodiments, the delivery system may be used to automatically adjust an electrical stimulation signal to optimize the treatment outcome in response to receiving a specific parameter (e.g., biomarker, time, volume, dosage, pH, etc.) measured over time.

It should be noted that the delivery system according to the present invention may include a general purpose computer, a specially programmed special purpose computer, or a microprocessor embedded in the system. A user may interact with the system via e.g., a personal computer or over PDA, e.g., the Internet, an Intranet, or embedded web interface, etc. Either of these may be implemented as a distributed computer system rather than a single computer. Similarly, the communications link may be a wireless link, a dedicated link, a modem over a POTS line, the Internet and/or any other method of communicating between computers and/or users. Moreover, the processing could be controlled by a software program on one or more computer systems or processors (e.g., without the electrical stimulator component, etc.), or could even be partially or wholly implemented in hardware.

It should be noted that the resulting delivery system may be implemented as an electronic component that is optimized for size, cost and performance and constitutes a main building block for various delivery devices. Alternatively, the delivery system may also be available as an electronic component with a sensor input and a feedback loop.

It is to be understood that the invention is not limited in its application to the details of construction and to the arrangements of the components and systems set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Although the present invention has been described and illustrated in the foregoing exemplary embodiments, it is understood that the present disclosure has been made only by way of example, and that numerous changes in the details of implementation of the invention may be made without departing from the spirit and scope of the invention, which is limited only by the claims which follow.

What is claimed is:
1. An apparatus for performing multiple diagnostics, the apparatus comprising:
a plurality of data acquisition modules that are simultaneously available to a patient and connected to a plurality of data processing modules, wherein the plurality of data acquisition modules simultaneously obtain a plurality of data that each include at least one of measurement data and biomarker data from a plurality of input sources associated directly with measurements made in the patient and simultaneously transmit each of the obtained plurality of data that includes at least one of measurement data and biomarker data relating to the patient to a corresponding data processing module from the plurality of data processing modules;
a treatment output module connected to one or more of the plurality of data processing modules that causes one or more treatment regimens for the patient to be administered, wherein the one or more treatment regimens for the patient are determined based on the obtained data that includes at least one of measurement data and biomarker data from the plurality of data acquisition modules;

a user control module connected to the plurality of data processing modules; and wherein the plurality of data processing modules generate patient information needed by the treatment output module.

2. The apparatus of claim 1 further comprising:

a user display system connected to the plurality of data processing modules, wherein the plurality of data processing modules being responsive to the user control module for generating the patient information and for generating user display information for use by the user display system.

3. The apparatus of claim 1, wherein the plurality of data acquisition modules sends the plurality of data that includes at least one of measurement data and biomarker data relating to a single disease to the plurality of data processing modules.

4. The apparatus of claim 1, wherein the plurality of data acquisition modules sends the plurality of data that includes at least one of measurement data and biomarker data relating to multiple diseases to the plurality of data processing modules.

5. The apparatus of claim 1 further comprising:

measuring modules, connected to the plurality of data acquisition modules, comprising one or more of: one or more biomarker sensors, a pH sensor, a $pO_2$ sensor, a spectrometer, an optical sensor, and an electrical measurement system, a chemical measurement system, a physical measurement system, and an electrochemical measurement system.

6. The apparatus of claim 1, wherein the plurality of data that includes at least one of measurement data and biomarker data are received from at least one of: a biosensor, a pH sensor, a $pO_2$ sensor, spectroscopy, an optical sensor, an electrical measurement system, a chemical measurement system, a physical measurement system, and an electrochemical measurement system.

7. The apparatus of claim 6, wherein the spectroscopy is selected from at least one of: fluorescent spectroscopy, mass spectroscopy, Raman spectroscopy, and Fourier transform infrared spectroscopy.

8. The apparatus of claim 1, further comprising a communications module that communicates with an external database for at least one of: receiving the patient information, receiving treatment protocols, receiving treatment information, storing the patient information, storing the treatment information, managing the patient information, managing the treatment information, and managing the treatment.

9. The apparatus of claim 8, wherein the communications are conducted using a secure protocol.

10. The apparatus of claim 8, wherein the external database provides at least a portion of the patient information and wherein the treatment output module uses the portion of the patient information for generating the treatment information.

11. The apparatus of claim 1, further comprising a wireless communications module that communicates with an external device.

12. The apparatus of claim 11, wherein the wireless communications module is configured to transmit at least one of: the plurality of data, updated data, the patient information, and the generated treatment information for display.

13. The apparatus of claim 11, wherein the wireless communications module and the external device are configured to allow a user to manually control at least one of drug delivery, electrical signal parameters, and treatment protocols.

14. The apparatus of claim 1, wherein each of the one of more data processing modules transmits the portion of the data to a single processing module for subsequent processing.

15. The apparatus of claim 1, wherein the plurality of data is measured in real time and simultaneously.

16. A method for performing multiple diagnostics, the method comprising:

simultaneously obtaining, using a plurality of data acquisition modules that are simultaneously available to a patient and connected to a plurality of data processing modules, a plurality of data that each include at least one of measurement data and biomarker data from a plurality of inputs sources associated directly with measurements made in the patient;

simultaneously transmitting each of the obtained data that includes at least one of measurement data and biomarker data relating to the patient to a corresponding data processing module from the plurality of data processing modules;

in response to the obtained data that includes at least one of measurement data and biomarker data, determining a diagnosis or treatment of a disease associated with the patient; and causing one or more treatment regimens for the patient to be administered based on the determined diagnosis or treatment, wherein the one or more treatment regimens for the patient are determined based on the obtained data that includes at least one of measurement data and biomarker data from the plurality of data acquisition modules.

17. The method of claim 16, further comprising:

selecting a plurality of the parameters to measure in response to a user input; and displaying to the user, a diagnosis and a basis therefore.

18. The method of claim 16, further comprising:

in response to further measurements of the parameters, determining an effectiveness of the treatment, and modifying, as necessary, the treatment regimen; and monitoring, on an on-going basis, the effectiveness of the treatment.

19. The method of claim 16, further comprising:

in response to the further measurements of the parameters, modifying, as necessary, the treatment regimen.

20. An apparatus for performing multiple diagnostics, the apparatus comprising:

a data acquisition module that is available to a patient and that is connected to a plurality of data processing modules, wherein the data acquisition module serially obtains, simultaneously in terms of body function, a plurality of data that each include at least one of measurement data and biomarker data from one or more input sources associated directly with measurements made in the patient and simultaneously transmits each of the obtained plurality of data that includes at least one of measurement data and biomarker data relating to the patient to a corresponding data processing module from the plurality of data processing modules;

a treatment output module connected to the data processing module that causes one or more treatment regimens for the patient to be administered, wherein the one or more treatment regimens for the patient are determined based on the obtained data that includes at least one of measurement data and biomarker data from the data acquisition module;

a user control module connected to the data processing module; and wherein the data processing module generates patient information needed by the treatment output module.

\* \* \* \* \*